United States Patent [19]
Casey

[11] Patent Number: 5,908,864
[45] Date of Patent: Jun. 1, 1999

[54] CREATINE GEL

[75] Inventor: Theodore R. Casey, Dallas, Tex.

[73] Assignee: Dymatize Enterprises, Carrollton, Tex.

[21] Appl. No.: 09/086,934

[22] Filed: May 28, 1998

[51] Int. Cl.$^6$ .................................................. A61K 31/195
[52] U.S. Cl. .......................... 514/564; 514/565; 514/944
[58] Field of Search ..................... 514/565, 564, 514/944

[56] References Cited

U.S. PATENT DOCUMENTS

| | | | |
|---|---|---|---|
| 4,740,458 | 4/1988 | Kondo et al. | 435/15 |
| 5,298,406 | 3/1994 | Loyd et al. | 435/17 |
| 5,451,520 | 9/1995 | Furukawa et al. | 435/227 |
| 5,612,375 | 3/1997 | Sueoka | 514/565 |
| 5,700,653 | 12/1997 | Lu et al. | 435/15 |

*Primary Examiner*—Frederick Krass
*Attorney, Agent, or Firm*—Steven W. Smith

[57] ABSTRACT

A nutritional gel containing creatine and the method of producing the creatine gel. The creatine gel is made by cross linking maltodextrin and a modified starch through an aqueous endothermal reaction at a temperature of approximately 90 degrees Celsius. A buffering agent, such as potassium phosphate, is added to the gel to maintain a pH value at approximately 7.0. The gel is then cooled and creatine is added. Next, the gel is stabilized bacteriologically by adding a preservative, such as potassium sorbate to the gel.

9 Claims, 1 Drawing Sheet

CREATINE GEL

BACKGROUND OF THE INVENTION

1. Technical Field of the Invention

This invention relates to nutritional supplements, and more particularly, to a nutritional gel containing creatine and the method of producing the creatine gel.

2. Description of Related Art

Nutritional supplementation is used by many people for a wide variety of reasons, such as improving one's diet, increasing one's exercise output, and preventing various ailments. Recently, one of the most popular supplements is creatine.

Creatine is a nutrient which is found in many foods and is stored within a human body's muscle cells. Creatine is one of the main sources of energy for muscles. Humans receive most of the creatine they need from food or dietary supplements. When a person does not consume enough creatine to meet the body's requirements, creatine production occurs in the liver, pancreas and kidneys.

Creatine is important for providing an energy source for muscular contractions. When a person's muscles contract, the initial fuel source is a chemical compound called adenosine triphosphate (ATP). ATP provides the energy to contract a person's muscles by releasing one of its phosphate molecules. The ATP then converts to another chemical compound, adenosine diphosphate (ADP). The energy produced from the release of the phosphate molecules lasts only about ten seconds, therefore, more ATP must be expended for continued muscle contraction. Creatine provides the source for replacing the missing phosphate molecules for ADP to convert to ATP, thereby providing the energy source necessary for continued muscular activity. Once the creatine provides the phosphate molecule to the ADP compound forming ATP, the newly reformed ATP may be re-used again.

The ability to regenerate ATP depends primarily on the body's supply of creatine. The more creatine available in the person's body, the more ATP remade, and the greater the ability for the person to use his muscles. This greater ability to use one's muscles is highly advantageous to a training athlete. Providing an increased supply of nutrients necessary to expend energy results in greater performance results during training.

Another energy source comes from glycolysis, which forms lactic acid as a by-product. This lactic acid creates the burning sensation a person feels in his muscles during intense exercise. If the amount of lactic acid becomes too great, muscle movement stops. However, when a person continues to use ATP as the primary energy source, other energy sources are minimized, such as from glycolysis. Thus, by using ATP, instead of utilizing the glycolysis process, lactic acid production is minimized, enabling a person to exercise longer and harder.

Therefore, creatine supplementation is very beneficial to a training athlete. Increased performance through creatine dietary supplementation is well known throughout the sports world. However, there are several problems in using creatine. First, creatine converts to creatinine over a period of time. Creatinine cannot be used to supplement the additional phosphate necessary to form ATP, therefore is not a useful supplement. Creatine converts to creatinine at a greater rate when it is mixed with water, or any other soluble liquid. Because of the instability of creatine within liquids, creatine is presently offered to users in only two forms, pills and powder.

Creatine powder has some disadvantages. A user must have a container and some liquid for mixing with the creatine powder. When the user desires to ingest the creatine powder, usually right before exercising, he must mix the creatine powder and the liquid in the container. This process can be time consuming and messy, and may result in spillage during the transfer of the creatine powder into its container.

Creatine pills are not always the optimum method of dietary supplementation. Many people have difficulty swallowing pills. Additionally, if a person chews the pills, the creatine may not be fully absorbed prior to the person commencing exercising. Pills also have the added disadvantage of having a bitter taste.

Although there are no known prior art teachings of a solution to the aforementioned deficiency and shortcoming such as that disclosed herein, a prior art reference that discusses subject matter that bears some relation to matters discussed herein is U.S. Pat. No. 5,612,375 to Sueoka (Sueoka). Sueoka discloses a process for producing a beverage comprising creatine as a main ingredient. The process comprises the steps of heating water rendered weakly alkaline and adding between one and three grams per 100 cc of a crystalline creatine powder to the heated water. Next, the creatine powder is dissolved by stirring the creatine powder into the heated water, forming a creatine aqueous solution. Then an additive is added to the creatine aqueous solution for improving the taste. Finally the creatine aqueous solution is sterilized to obtain a creatine beverage having a pH value between 7 and 10. However, Sueoka merely discloses a creatine liquid. Sueoka does not teach or suggest a creatine supplement which prevents the rapid conversion of creatine to creatinine.

Thus, it would be a distinct advantage to have a creatine supplement which does not quickly convert to creatinine and is easily and conveniently ingested by a person. It is an object of the present invention to provide such a supplement and method of producing it.

SUMMARY OF THE INVENTION

In one aspect, the present invention is a creatine gel which is produced by a process. The process includes creating a gel. The gel is formed by cross linking maltodextrin and a modified starch through an aqueous endothermal reaction between a temperature range of 70 and 100 degrees Celsius. Next, a buffering agent is added to the gel to maintain a pH value of approximately 7.0 within the gel. Creatine is then added to the gel. The gel is stabilized bacteriologically by adding a preservative to the gel.

In another aspect, the present invention is a process for producing a creatine gel. The process begins by creating a gel. The gel is formed through an aqueous endothermal reaction between a temperature range of 70 and 100 degrees Celsius. Next, a buffering agent is added to the gel to maintain a pH value of approximately 7.0 within the gel. The creatine is then added to the gel. The gel is then stabilized bacteriologically by adding a preservative to the gel.

In still another aspect, the present invention is a process for producing a creatine gel. The process begins by creating a gel. The gel is formed by cross linking maltodextrin and a modified starch through an aqueous endothermal reaction at a temperature of approximately 90 degrees Celsius. Next, a buffering agent is added to the gel to maintain a pH value of approximately 7.0 within the gel. The gel is then cooled. Then, creatine is added to the gel and stabilized bacteriologically by adding a preservative to the gel.

BRIEF DESCRIPTION OF THE DRAWINGS

The invention will be better understood and its numerous objects and advantages will become more apparent to those skilled in the art by reference to the following drawing, in conjunction with the accompanying specification, in which.

DETAILED DESCRIPTION OF EMBODIMENTS

Figure 1:
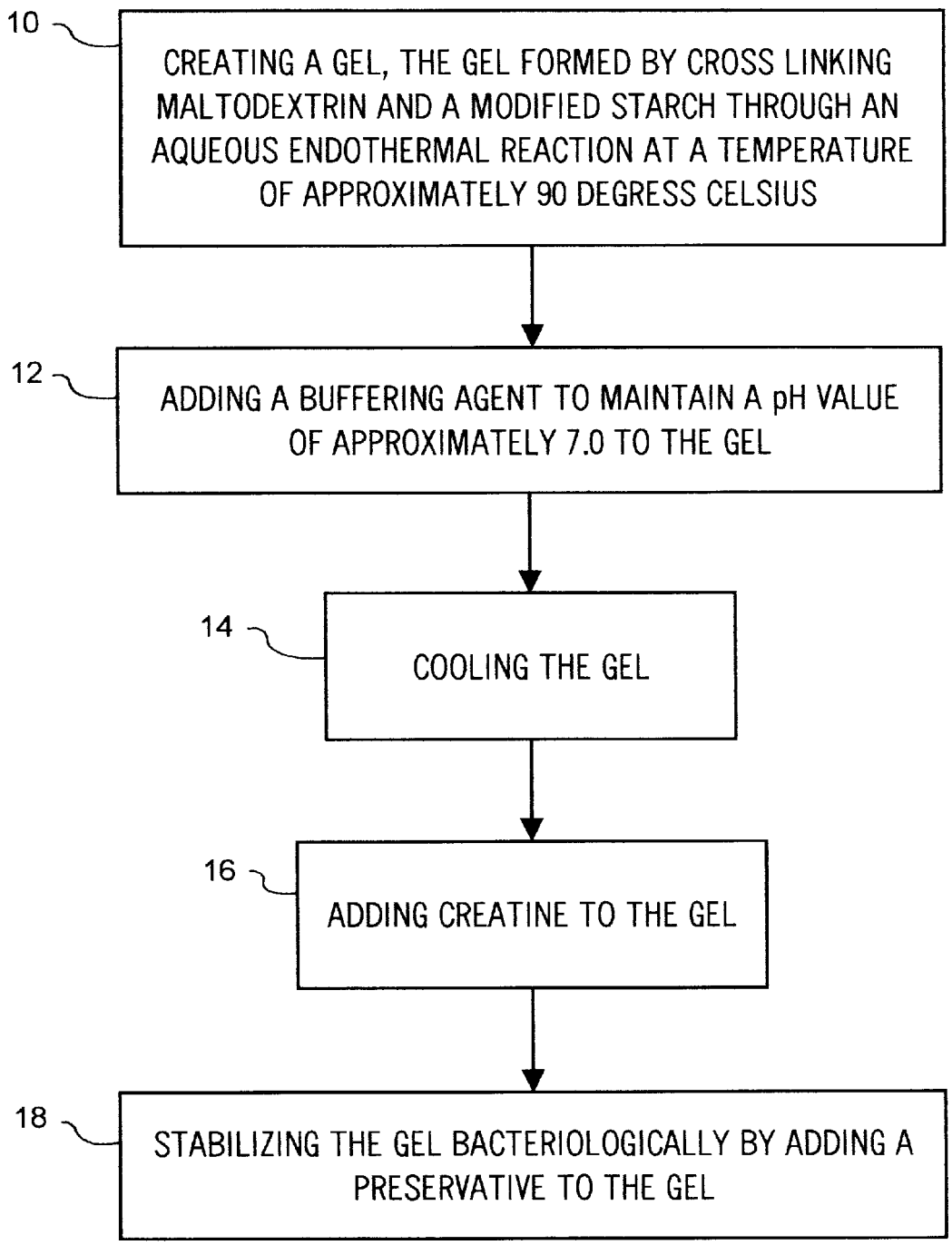
FIG. 1 is a flowchart illustrating the steps for producing a creatine gel in accordance with the preferred embodiment of the present invention.

The present invention is a nutritional gel containing creatine, and the method of producing the creatine gel.

Creatine converts to creatinine over at period of time. Additionally, the conversion rate of creatine to creatinine is typically increased when mixed with a soluble liquid. The creatine conversion rate is very pH dependent, with greater stability achieved at a higher pH value. Optimally, to produce a creatine gel, maximum chemical stability is achieved at a pH value of approximately 7.0 (pH value between 6.5 and 8.0).

FIG. 1 is a flowchart illustrating the steps for producing a creatine gel. In step 10, a gel is created by cross linking maltodextrin and modified starch (e.g., corn starch) through an aqueous endothermal reaction at approximately 90 degrees Celsius. In alternate embodiments of the present invention, other chemicals such as xanthan gum, acacia gum or arabic gum may be used instead of maltodextrin. However, a temperature range from 70 to 100 degrees Celsius may be used.

Next, in step 12, a buffer of potassium phosphate is added to the gel to maintain a pH value of approximately 7.0 (pH value between 6.5 and 8.0). Although potassium phosphate is the preferred buffer, other chemicals may be used, such as mono-sodium-citrates, di-sodium-citrates, tri-sodium-citrates, sodium-malate, potassium-malate, calcium malate, mono-sodium L-(+)-tartrate, and di-sodium L-(+)-tartrate.

In step 14, the gel is preferably cooled to a temperature between 45 and 55 degrees Celsius. Bacteria may form below 45 degrees Celsius. If the gel is cooled to a higher temperature than 55 degrees Celsius, the gel remains a liquid rather than a gel. Next, in step 16, creatine is added to the gel. The creatine is preferably added to the gel after it is cooled to prevent excessive degradation of creatine to creatinine. The gel may also be formed by utilizing pre-gelatinized starches at low temperatures. However, gels using these pre-gelatinized starches are less stable and may encourage bacteriological problems in a finished product.

In step 18, the gel is stabilized bacteriologically. In the preferred embodiment, the preferred preservative is potassium-sorbate. However, in alternate embodiments, other preservatives may be used, such as sodium-sorbate, calcium-propionate, potassium-propionate, sodium L-ascorbate, and calcium-benzoate.

The creatine gel provides many benefits. The gel is easily ingested by a person. There is no preparation necessary prior to using the gel. In addition, the creatine gel converts from creatine to creatinine at a very slow rate, allowing for a longer shelve-life of the creatine gel.

It is thus believed that the operation and construction of the present invention will be apparent from the foregoing description. While the method and gel shown and described has been characterized as being preferred, it will be readily apparent that various changes and modifications could be made therein without departing from the spirit and scope of the invention as defined in the following claims.

What is claimed is:

1. A creatine gel which is produced by a process comprising the steps of:

creating a gel, the gel formed by cross linking maltodextrin and a modified starch through an aqueous endothermal reaction conducted between a temperature range of 70 and 100 degrees Celsius;

adding a buffering agent to maintain a pH value of approximately 7.0 within the gel;

adding creatine to the gel; and stabilizing the gel bacteriologically by adding a preservative to the gel.

2. The creatine gel of claim 1 produced by a process further comprising, after the step of creating a gel, the step of cooling the gel.

3. The creatine gel of claim 1 wherein the step of adding a buffering agent includes adding a buffering agent selected from the group consisting of: potassium phosphate; mono-sodium-citrate; di-sodium-citrate; tri-sodium-citrate; sodium-malate; potassium-malate; calcium-malate; mono-sodium L-(+)-tartrate; and di-sodium L-(+)-tartrate.

4. The creatine gel of claim 1 wherein the step of stabilizing the gel bacteriologically includes adding a preservative selected from the group consisting of: sodium-sorbate; potassium-sorbate; calcium-propionate; potassium-propionate; sodium L-ascorbate; and calcium-benzoate.

5. A process for producing a creatine gel comprising the steps of:

creating a gel, the gel formed through an aqueous endothermal reaction crosslinking conducted between a temperature range of 70 and 100 degrees Celsius;

adding a buffering agent to maintain a pH value of approximately 7.0 within the gel;

adding creatine to the gel; and stabilizing the gel bacteriologically by adding a preservative to the gel.

6. The process for producing a creatine gel of claim 5 wherein the step of creating a gel includes the step of cross linking maltodextrin and a modified starch.

7. The process for producing a creatine gel of claim 5 further comprising, after the step of creating the gel, the step of cooling the gel.

8. The process for producing a creatine gel of claim 5 wherein the step of creating a gel includes the step of cross linking a chemical substance selected from the group consisting of: xanthan gum; acacia gum; and arabic gum with corn starch.

9. A process for producing a creatine gel comprising the steps of:

creating a gel, the gel formed by cross linking maltodextrin and a modified starch through an aqueous endothermal reaction conducted at a temperature of approximately 90 degrees Celsius;

adding a buffering agent to maintain a pH value of approximately 7.0 to the gel;

cooling the gel;

adding creatine to the gel; and stabilizing the gel bacteriologically by adding a preservative to the gel.

\* \* \* \* \*